United States Patent
Chin et al.

(10) Patent No.: US 7,720,516 B2
(45) Date of Patent: *May 18, 2010

(54) MOTION COMPATIBLE SENSOR FOR NON-INVASIVE OPTICAL BLOOD ANALYSIS

(75) Inventors: Rodney Chin, Oakland, CA (US); Paul Mannheimer, Danville, CA (US); Ross Flewelling, Oakland, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1583 days.

This patent is subject to a terminal disclaimer.

(21) Appl. No.: 10/990,686

(22) Filed: Nov. 16, 2004

(65) Prior Publication Data

US 2005/0070773 A1     Mar. 31, 2005

Related U.S. Application Data

(60) Continuation of application No. 10/080,433, filed on Feb. 21, 2002, now Pat. No. 6,845,256, which is a division of application No. 09/348,437, filed on Jul. 7, 1999, now Pat. No. 6,374,129, which is a division of application No. 08/722,443, filed on Oct. 10, 1996, now Pat. No. 6,018,673.

(51) Int. Cl.
*A61B 5/1455* (2006.01)
(52) U.S. Cl. ..................... 600/322; 600/323
(58) Field of Classification Search ............ 600/310, 600/322, 323, 336; 702/189, 190
See application file for complete search history.

(56) References Cited

U.S. PATENT DOCUMENTS

| 3,090,377 A | 5/1963 | Salisbury et al. |
| 3,095,872 A | 7/1963 | Tolles |
| 3,638,640 A | 2/1972 | Shaw |
| 4,714,341 A | 12/1987 | Hamaguri et al. |
| 4,802,486 A | 2/1989 | Goodman et al. |
| 4,805,623 A | 2/1989 | Jöbsis |

(Continued)

FOREIGN PATENT DOCUMENTS

DE     19640807     9/1997

(Continued)

OTHER PUBLICATIONS

Odell, Richard M. et al., "Use of pulse oximetry to monitor venous saturation during extracorporeal life support", *Critical Care Medicine*, vol. 22, No. 4, 1994.

(Continued)

*Primary Examiner*—Eric F Winakur
*Assistant Examiner*—Etsub D Berhanu
(74) *Attorney, Agent, or Firm*—Fletcher Yoder

(57) ABSTRACT

A non-invasive optical sensor which uses the motion signal to calculate the physiological characteristic being measured. For pulse oximetry, a least squares or a ratio-of-ratios technique can be applied to the motion signal itself. This is made possible by selecting a site on the patient where variations in motion produce signals of two wavelengths which are sufficiently correlated. In particular, it has been determined that a sensor placed on a nail, in particular a thumbnail, exhibits the characteristics of having the red and infrared signals correlated when used for pulse oximetry, and the resulting signals correlate to arterial oxygen saturation.

9 Claims, 10 Drawing Sheets

U.S. PATENT DOCUMENTS

| | | |
|---|---|---|
| 4,807,631 A | 2/1989 | Hersh et al. |
| 4,832,484 A | 5/1989 | Aoyagi et al. |
| 4,869,254 A | 9/1989 | Stone et al. |
| 4,869,261 A | 9/1989 | Peñáz |
| 4,883,055 A | 11/1989 | Merrick |
| 4,883,353 A | 11/1989 | Hausman et al. |
| 4,901,238 A | 2/1990 | Suzuki et al. |
| 4,911,167 A | 3/1990 | Corenman et al. |
| 4,913,150 A | 4/1990 | Cheung et al. |
| 4,927,264 A | 5/1990 | Shiga et al. |
| 4,934,372 A | 6/1990 | Corenman et al. |
| 4,936,679 A | 6/1990 | Mersch |
| 4,938,218 A | 7/1990 | Goodman et al. |
| 4,955,379 A | 9/1990 | Hall |
| 4,960,126 A * | 10/1990 | Conlon et al. ............... 600/336 |
| 4,971,062 A | 11/1990 | Hasebe et al. |
| 4,972,331 A | 11/1990 | Chance |
| 4,974,591 A | 12/1990 | Awazu et al. |
| 5,025,791 A | 6/1991 | Niwa |
| 5,028,787 A | 7/1991 | Rosenthal et al. |
| 5,055,671 A | 10/1991 | Jones |
| 5,065,749 A | 11/1991 | Hasebe et al. |
| 5,078,136 A | 1/1992 | Stone et al. |
| 5,084,327 A | 1/1992 | Stengel |
| 5,099,842 A | 3/1992 | Mannheimer et al. |
| 5,111,817 A | 5/1992 | Clark et al. |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,218,962 A | 6/1993 | Mannheimer et al. |
| 5,226,417 A | 7/1993 | Swedlow et al. |
| 5,246,003 A | 9/1993 | DeLonzor |
| 5,247,931 A | 9/1993 | Norwood |
| 5,263,244 A | 11/1993 | Centa et al. |
| 5,267,563 A | 12/1993 | Swedlow et al. |
| 5,267,565 A | 12/1993 | Beard |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,297,548 A | 3/1994 | Pologe |
| 5,343,867 A | 9/1994 | Shankar |
| 5,351,685 A | 10/1994 | Potratz |
| 5,355,880 A | 10/1994 | Thomas et al. |
| 5,355,882 A | 10/1994 | Ukawa et al. |
| 5,368,026 A | 11/1994 | Swedlow et al. |
| 5,372,136 A | 12/1994 | Steuer et al. |
| 5,385,143 A | 1/1995 | Aoyagi |
| 5,390,670 A | 2/1995 | Centa et al. |
| 5,392,777 A | 2/1995 | Swedlow et al. |
| 5,398,680 A | 3/1995 | Polson et al. |
| 5,413,099 A | 5/1995 | Schmidt et al. |
| 5,421,329 A | 6/1995 | Casciani et al. |
| 5,431,170 A | 7/1995 | Mathews |
| 5,452,717 A | 9/1995 | Branigan et al. |
| 5,469,845 A | 11/1995 | DeLonzor et al. |
| RE35,122 E | 12/1995 | Corenman |
| 5,482,036 A | 1/1996 | Diab et al. |
| 5,483,646 A | 1/1996 | Uchikoga |
| 5,485,847 A * | 1/1996 | Baker, Jr. .................... 600/323 |
| 5,490,505 A | 2/1996 | Diab |
| 5,499,627 A | 3/1996 | Steuer |
| 5,503,148 A | 4/1996 | Pologue et al. |
| 5,517,988 A | 5/1996 | Gerhard |
| 5,524,617 A | 6/1996 | Mannheimer |
| 5,553,614 A | 9/1996 | Chance |
| 5,555,882 A | 9/1996 | Richardson |
| 5,564,417 A | 10/1996 | Chance |
| 5,575,285 A | 11/1996 | Takanashi et al. |
| 5,588,425 A | 12/1996 | Sackner et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,611,337 A | 3/1997 | Bukta |
| 5,617,852 A | 4/1997 | Macgregor |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,645,059 A | 7/1997 | Fein et al. |
| 5,645,060 A | 7/1997 | Yorkey |
| 5,662,106 A | 9/1997 | Swedlow et al. |
| 5,676,141 A | 10/1997 | Hollub |
| 5,680,857 A | 10/1997 | Pelikan et al. |
| 5,685,299 A | 11/1997 | Diab et al. |
| 5,687,719 A | 11/1997 | Sato et al. |
| 5,687,722 A | 11/1997 | Tien et al. |
| 5,692,503 A | 12/1997 | Keunstner |
| 5,692,505 A | 12/1997 | Fouts |
| 5,713,355 A | 2/1998 | Richardson |
| 5,730,124 A | 3/1998 | Yamauchi |
| 5,731,582 A | 3/1998 | West |
| 5,743,263 A | 4/1998 | Baker, Jr. |
| 5,746,206 A | 5/1998 | Mannheimer |
| 5,758,644 A | 6/1998 | Diab et al. |
| 5,769,785 A | 6/1998 | Diab et al. |
| 5,776,059 A | 7/1998 | Kaestle et al. |
| 5,779,631 A | 7/1998 | Chance |
| 5,782,757 A | 7/1998 | Diab et al. |
| 5,786,592 A | 7/1998 | Hök |
| 5,792,050 A | 8/1998 | Alam et al. |
| 5,803,908 A | 9/1998 | Steuer et al. |
| 5,817,009 A | 10/1998 | Rosenheimer |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,846,190 A | 12/1998 | Woehrle |
| 5,853,364 A | 12/1998 | Baker et al. |
| 5,860,919 A | 1/1999 | Kiani-Azarbayjany et al. |
| 5,871,442 A | 2/1999 | Madarasz et al. |
| 5,873,821 A | 2/1999 | Chance et al. |
| 5,879,373 A | 3/1999 | Roper et al. |
| 5,885,213 A | 3/1999 | Richardson et al. |
| 5,920,263 A | 7/1999 | Huttenhoff et al. |
| 5,934,277 A | 8/1999 | Mortz |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,018,673 A | 1/2000 | Chin et al. |
| 6,022,321 A | 2/2000 | Amano et al. |
| 6,036,642 A | 3/2000 | Diab et al. |
| 6,064,898 A | 5/2000 | Aldrich |
| 6,081,735 A | 6/2000 | Diab et al. |
| 6,081,742 A | 6/2000 | Amano et al. |
| 6,083,172 A | 7/2000 | Baker et al. |
| 6,088,607 A | 7/2000 | Diab et al. |
| 6,104,938 A | 8/2000 | Huiku et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,157,850 A | 12/2000 | Diab et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,206,830 B1 | 3/2001 | Diab et al. |
| 6,217,523 B1 | 4/2001 | Amano et al. |
| 6,222,189 B1 | 4/2001 | Misner et al. |
| 6,230,035 B1 | 5/2001 | Aoyagi et al. |
| 6,236,872 B1 | 5/2001 | Diab et al. |
| 6,263,222 B1 | 7/2001 | Diab et al. |

| | | |
|---|---|---|
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,385,471 B1 | 5/2002 | Mortz |
| 6,397,091 B2 | 5/2002 | Diab et al. |
| 6,411,832 B1 | 6/2002 | Guthermann |
| 6,411,833 B1 | 6/2002 | Baker et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,650,917 B2 | 11/2003 | Diab et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,681,128 B2 | 1/2004 | Steuer et al. |
| 6,684,090 B2 | 1/2004 | Ali et al. |
| 6,690,958 B1 | 2/2004 | Walker et al. |
| 6,697,658 B2 | 2/2004 | Al-Ali |
| RE38,476 E | 3/2004 | Diab et al. |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| RE38,492 E | 4/2004 | Diab et al. |
| 6,721,584 B2 | 4/2004 | Baker, Jr. et al. |
| 6,731,274 B2 | 5/2004 | Powell |
| 6,745,060 B2 | 6/2004 | Diab et al. |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,826,419 B2 | 11/2004 | Diab et al. |
| 6,829,496 B2 | 12/2004 | Nagai et al. |
| 6,836,679 B2 | 12/2004 | Baker et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,931,268 B1 | 8/2005 | Kiani-Azarbayjany et al. |
| 6,939,305 B2 | 9/2005 | Flaherty et al. |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,041,060 B2 | 5/2006 | Flaherty et al. |
| 7,047,056 B2 | 5/2006 | Hannula et al. |
| 7,127,278 B2 | 10/2006 | Melker et al. |
| 7,162,306 B2 | 1/2007 | Caby et al. |
| 7,209,775 B2 | 4/2007 | Bae et al. |
| 7,215,984 B2 | 5/2007 | Diab et al. |
| 7,215,986 B2 | 5/2007 | Diab et al. |
| 7,236,811 B2 | 6/2007 | Schmitt |
| 7,239,905 B2 | 7/2007 | Kiani-Azarbayjany et al. |
| 7,263,395 B2 | 8/2007 | Chan et al. |
| 7,272,426 B2 | 9/2007 | Schmid |
| 7,315,753 B2 | 1/2008 | Baker et al. |
| 7,328,053 B1 | 2/2008 | Diab et al. |
| 7,336,983 B2 | 2/2008 | Baker et al. |
| 7,373,193 B2 | 5/2008 | Al-Ali et al. |
| 7,376,453 B1 | 5/2008 | Diab et al. |
| 7,383,070 B2 | 6/2008 | Diab et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0128544 A1 | 9/2002 | Diab et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0158135 A1 | 8/2004 | Baker et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0181134 A1 | 9/2004 | Baker et al. |
| 2004/0204636 A1 | 10/2004 | Diab et al. |
| 2004/0204638 A1 | 10/2004 | Diab et al. |
| 2004/0210146 A1 | 10/2004 | Diab et al. |
| 2004/0230106 A1 | 11/2004 | Schmitt et al. |
| 2004/0236196 A1 | 11/2004 | Diab et al. |
| 2005/0080323 A1 | 4/2005 | Kato |
| 2005/0085735 A1 | 4/2005 | Baker, Jr. et al. |
| 2005/0101850 A1 | 5/2005 | Parker |
| 2005/0113651 A1 | 5/2005 | Wood et al. |
| 2005/0113656 A1 | 5/2005 | Chance |
| 2005/0143634 A1 | 6/2005 | Baker, Jr. et al. |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |

| | | |
|---|---|---|
| 2005/0209517 A1 | 9/2005 | Diab et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0217609 A1 | 9/2006 | Diab et al. |
| 2006/0224058 A1 | 10/2006 | Mannheimer |
| 2006/0247501 A1 | 11/2006 | Ali |
| 2006/0258921 A1 | 11/2006 | Addison et al. |
| 2007/0225581 A1 | 9/2007 | Diab et al. |
| 2007/0249918 A1 | 10/2007 | Diab et al. |
| 2007/0291832 A1 | 12/2007 | Diab et al. |
| 2008/0004514 A1 | 1/2008 | Diab et al. |
| 2008/0033266 A1 | 2/2008 | Diab et al. |
| 2008/0045823 A1 | 2/2008 | Diab et al. |

FOREIGN PATENT DOCUMENTS

| | | |
|---|---|---|
| EP | 0615723 | 9/1994 |
| EP | 0630203 | 12/1994 |
| EP | 734223 | 5/1998 |
| EP | 1491135 | 12/2004 |
| JP | 63275325 | 11/1988 |
| JP | 3170866 | 7/1991 |
| JP | 4191642 | 7/1992 |
| JP | 4332536 | 11/1992 |
| JP | 6285048 | 10/1994 |
| JP | 7124138 | 5/1995 |
| JP | 7136150 | 5/1995 |
| JP | 7171139 | 7/1995 |
| JP | 10216115 | 8/1998 |
| JP | 3238813 | 10/2001 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 | 7/2004 |
| JP | 2004202190 | 7/2004 |
| JP | 2004248819 | 9/2004 |
| JP | 2004290545 | 10/2004 |
| JP | 2005034472 | 2/2005 |
| WO | WO9101678 | 2/1991 |
| WO | WO9111137 A1 | 8/1991 |
| WO | WO92/16142 | 10/1992 |
| WO | WO92/21281 | 12/1992 |
| WO | WO9221281 | 12/1992 |
| WO | WO9309711 | 5/1993 |
| WO | WO9403102 | 2/1994 |
| WO | WO9423643 A1 | 10/1994 |
| WO | WO9512349 | 5/1995 |
| WO | WO9516388 | 6/1995 |
| WO | WO96/39926 | 12/1996 |
| WO | WO9639927 | 12/1996 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO0140776 | 6/2001 |
| WO | WO0176461 | 10/2001 |
| WO | WO0176471 | 10/2001 |
| WO | WO03039326 | 5/2003 |
| WO | WO2005009221 | 2/2005 |

OTHER PUBLICATIONS

Inoue, Hajimi, "Three-dimensional observations of microvasculature of human finger skin", *The Hand*, vol. 10, No. 2, 1978.

*Atlas of Human Anatomy*, "Systemic anatomy", Frick, Kummer, Putz ed., Karger, Basel, Switzerland, 1990.

"Sensor für durchführung medizinischer messungen, insbesondere pulsoximetrischer messungen, am menschlichen finger", Research Disclosure, Dec. 1995, pp. 831-832.

S. Takatani et al., "A non-invasive reflectance pulse oximeter sensor", Annual International Conference of the IEEE Engineering in Medicine and Biology Society, vol. 13, No. 4, 1991.

Aoyagi T. et al.; "Analysis of Motion Artifacts in Pulse Oximetry" *Japanese Society ME* vol. 42 p. 20 (1993) (Article in Japanese—contains English summary of article).

Barreto A.B. et al.; "Adaptive Cancelation of Motion artifact in Photoplethysmographic Blood Volume Pulse Measurements for Exercise Evaluation" *IEEE-EMBC and CMBEC—Theme 4: Signal Processing* pp. 983-984 (1995).

Vincente L.M. et al.; "Adaptive Pre-Processing of Photoplethysmographic Blood Volume Pulse Measurements" pp. 114-117 (1996).

Barreto Armando B. et al.; "Adaptive LMS Delay Measurement in dual Blood Volume Pulse Signals for Non-Invasive Monitoring" *IEEE* pp. 117-120 (1997).

Barnum P.T. et al.; "Novel Pulse Oximetry Technology Capable of Reliable Bradycardia Monitoring in the Neonate" *Respiratory Care* vol. 42 No. 1 p. 1072 (Nov. 1997).

Leahy Martin J. et al.; "Sensor Validation in Biomedical Applications" *IFAC Modelling and Control in Biomedical Systems* Warwick UK; pp. 221-226 (1997).

Masin Donald I. et al.; "Fetal Transmission Pulse Oximetry" *Proceedings 19th International Conference IEEE/EMBS* Oct. 30-Nov. 2, 1997; pp. 2326-2329.

Pickett John et al.; "Pulse Oximetry and PPG Measurements in Plastic Surgery" *Proceedings—19th International Conference—IEEE/EMBS* Chicago Illinois Oct. 30-Nov. 2, 1997 pp. 2330-2332.

Plummer John L. et al.; "Identification of Movement Artifact by the Nellcor N-200 and N-3000 Pulse Oximeters" *Journal of clinical Monitoring* vol. 13 pp. 109-113 (1997).

Poets C. F. et al.; "Detection of movement artifact in recorded pulse oximeter saturation" *Eur. J. Pediatr.*; vol. 156 pp. 808-811 (1997).

East Christine E. et al.; "Fetal Oxygen Saturation and Uterine Contractions During Labor" *American Journal of Perinatology* vol. 15 No. 6 pp. 345-349 (Jun. 1998).

Edrich Thomas et al.; "Can the Blood Content of the Tissues be Determined Optically During Pulse Oximetry Without Knowledge of the Oxygen Saturation?—An In-Vitro Investigation" *Proceedings of the 20th Annual International conference of the IEEE Engie in Medicine and Biology Society* vol. 20 No. 6 p. 3072-3075 1998.

Hayes Matthew J. et al.; "Quantitative evaluation of photoplethysmographic artifact reduction for pulse oximetry" *SPIE* vol. 3570 pp. 138-147 (Sep. 1998).

Hayes Matthew J. et al.; "Artifact reduction in photoplethysmography" *Applied Optics* vol. 37 No. 31 pp. 7437-7446 (Nov. 1998).

Such Hans Olaf; "Optoelectronic Non-invasive Vascular Diagnostics Using multiple Wavelength and Imaging Approach" *Dissertation* (1998).

Kaestle S.; "An Algorithm for Reliable Processing of Pulse Oximetry Signals Under strong Noise Conditions" *Dissertation Book* Lubeck University Germany (1999).

Rhee Sokwoo et al.; "Design of a Artifact-Free Wearable Plethysmographic Sensor" *Proceedings of the First joint BMES/EMBS Conference* Oct. 13-16, 1999 Altanta Georgia p. 786.

Rheineck-Leyssius Aart t. et al.; "Advanced Pulse Oximeter Signal Processing Technology Compared to Simple Averaging: I. Effect on Frequency of Alarms in the Operating Room" *Journal of clinical Anesthesia* vol. 11 pp. 192-195 (1999).

Seelbach-Göbel Birgit et al.; "The prediction of fetal acidosis by means of intrapartum fetal pulse oximetry" *Am J. Obstet. Gynecol.* vol. 180 No. 1 Part 1 pp. 73-81 (1999).

Todd Bryan et al.; "The Identification of Peaks in Physiological Signals" *Computers and Biomedical Research* vol. 32 pp. 322-335 (1999).

Coetzee Frans M.; "Noise-Resistant Pulse Oximetry Using a Synthetic Reference Signal" *IEEE Transactions on Biomedical Engineering* vol. 47 No. 8 Aug. 2000 pp. 1018-1026.

Goldman Julian M.; "Masimo Signal Extraction Pulse Oximetry" *Journal of Clinical Monitoring and Computing* vol. 16 pp. 475-483 (2000).

Kaestle S.; "Determining Artefact Sensitivity of New Pulse Oximeters in Laboratory Using Signals Obtained from Patient" *Biomedizinische Technik* vol. 45 (2000).

Nilsson Lena et al.; "Monitoring of Respiratory Rate in Postoperative Care Using a New Photoplethysmographic Technique" *Journal of Clinical Monitoring and Computing* vol. 16 pp. 309-315 (2000).

Tremper K.K.; "A Second Generation Technique for Evaluating Accuracy and Reliability of Second Generation Pulse Oximeters" *Journal of Clinical Monitoring and Computing* vol. 16 pp. 473-474 (2000).

Belal Suliman Yousef et al.; "A fuzzy system for detecting distorted plethysmogram pulses in neonates and paediatric patients" *Physiol. Meas.* vol. 22 pp. 397-412 (2001).

Cysewska-Sobusaik Anna; "Metrological Problems With noninvasive Transillumination of Living Tissues" *Proceedings of SPIE* vol. 4515 pp. 15-24 (2001).

Earthrowl-Gould T. et al.; "Chest and abdominal surface motion measurement for continuous monitoring of respiratory function" *Proc. Instn Mech Engrs* V215 Part H; pp. 515-520 (2001).

Hayes Matthew J. et al.; "A New Method for Pulse Oximetry Possessing Inherent Insensitivity to Artifact" *IEEE Transactions on Biomedical Engineering* vol. 48 No. 4 pp. 452-461 (Apr. 2001).

Maletras Francois-Xavier et al.; "Construction and calibration of a new design of Fiber Optic Respiratory Plethysmograph (FORP)" *Optomechanical Design and Engineering Proceedings of SPIE* vol. 4444 pp. 285-293 (2001).

Chan K.W. et al.; "17.3: Adaptive Reduction of Motion Artifact from Photoplethysmographic Recordings using a Variable Step-Size LMS Filter" *IEEE* pp. 1343-1346 (2002).

Gehring Harmut et al.; "The Effects of Motion Artifact and Low Perfusion on the Performance of a New Generation of Pulse Oximeters in Volunteers Undergoing Hypoxemia" *Respiratory Care* Vo. 47 No. 1 pp. 48-60 (Jan. 2002).

Gostt R. et al.; "Pulse Oximetry Artifact Recognition Algorithm for Computerized Anaesthetic Records" *Journal of Clinical Monitoring and Computing Abstracts* p. 471 (2002).

Jopling Michae W. et al.; "Issues in the Laboratory Evaluation of Pulse Oximeter Performance" *Anesth Analg* vol. 94 pp. S62-S68 (2002).

Relente A.R. et al.; "Characterization and Adaptive Filtering of Motion Artifacts in Pulse Oximetry using Accelerometers" *Proceedings of the Second joint EMBS/BMES Conference* Houston Texas Oct. 23-26, 2002; pp. 1769-1770.

Yamaya Yoshiki et al.; "Validity of pulse oximetry during maximal exercise in normoxia hypoxia and hyperoxia" *J. Appl. Physiol.* vol. 92 pp. 162-168 (2002).

Yao Jianchu et al.; "Design of a Plug-and-Play Pulse Oximeter" *Proceedings of the Second Joint EMBS/BMES Conference* Houston Texas Oct. 23-26, 2002; pp. 1752-1753.

Yoon Gilwon et al.; Multiple diagnosis based on Photoplethysmography: hematocrit SpO2 pulse and respiration *Optics in Health Care and Biomedical optics: Diagnostics and Treatment; Proceedings of the SPIE* vol. 4916; pp. 185-188 (2002).

Aoyagi Takuo; "Pulse oximetry: its invention theory and future" *Journal of Anesthesia* vol. 17 pp. 259-266 (2003).

Cyrill D. et al.; "Adaptive Comb Filter for Quasi-Periodic Physiologic Signals" *Proceedings of the 25th Annual International Conference of the IEEE EMBS* Cancun Mexico Sep. 17-21, 2003; pp. 2439-2442.

A. Johansson; "Neural network for photoplethysmographic respiratory rate monitoring" *Medical & Biological Engineering & Computing* vol. 41 pp. 242-248 (2003).

Lee C.M. et al.; "Reduction of motion artifacts from photoplethysmographic recordings using wavelet denoising approach" *IEEE EMBS Asian-Pacific Conference on Biomedical Engineering* Oct. 20-22, 2003; pp. 194-195.

Matthews Nora S. et al.; "An evaluation of pulse oximeters in dogs cats and horses" *Veterinary Anaesthesia and Analgesia* vol. 30 pp. 3-14 (2003).

Stetson Paul F.; "Determining Heart Rate from Noisey Pulse Oximeter Signals Using Fuzzy Logic" *The IEEE International Conference on Fuzzy Systems* St. Louis Missouri May 25-28, 2003; pp. 1053-1058.

Addison Paul S. et al.; "A novel time-frequency-based 3D Lissajous figure method and its application to the determination of oxygen saturation from the photoplethysmogram" *Institute of Physic Publishing Meas. Sci. Technol.* vol. 15 pp. L15-L18 (2004).

Johnston W.S. et al.; "Extracting Breathing Rate Infromation from a Wearable Reflectance Pulse Oximeter Sensor" *Proceedings of the 26th Annual International conference of the IEEE EMBS* San Francisco California; Sep. 1-5, 2004; pp. 5388-5391.

Spigulis Janis et al.; "Optical multi-channel sensing of skin blood pulsations" *Optical Sensing Proceedings of SPIE* vol. 5459 pp. 46-53 (2004).

Matsuzawa Y. et al.; "Pulse Oximeter" *Home Care Medicine* pp. 42-45 (Jul. 2004); (Article in Japanese—contains English summary of article).

Yao Jianchu et al.; "A Novel Algorithm to Separate Motion Artifacts from Photoplethysmographic Signals Obtained With a Reflectance Pulse Oximeter" *Proceedings of the 26th Annual International conference of the IEEE EMBS* San Francisco California Sep. 2004 pp. 2153-2156.

Yan Yong-sheng et al.; "Reduction of motion artifact in pulse oximetry by smoothed pseudo Wigner-Ville distribution" *Journal of NeuroEngineering and Rehabilitation* vol. 2 No. 3 (9 pages) (Mar. 2005).

Hamilton Patrick S. et al.; "Effect of Adaptive Motion-Artifact Reduction on QRS Detection" *Biomedical Instrumentation & Technology* pp. 197-202 (undated).

Kim J.M. et al.; "Signal Processing Using Fourier & Wavelet Transform" pp. II-310-II-311 (undated).

J. Huang et al.; "Low Power Motion Tolerant Pulse Oximetry" *Abstracts* A7 p. S103. (undated).

P. Lang et al.; "Signal Identification and Quality Indicator™ for Motion Resistant Pulse Oximetry" *Abstracts* A10 p. S105. (undated).

R. Neumann et al.; "Fourier Artifact suppression Technology Provides Reliable SpO$_2$" *Abstracts* A11 p. S105. (undated).

Odagiri Y.; "Pulse Wave Measuring Device" *Micromechatronics* vol. 42 No. 3 pp. 6-11 (undated) (Article in Japanese—contains English summary of article).

Yamazaki Nakaji et al.; "Motion Artifact Resistant Pulse Oximeter (Durapulse PA 2100)" *Journal of Oral Cavity Medicine* vol. 69 No. 4 pp. 53 (date unknown) (Article in Japanese—contains English summary of article).

* cited by examiner

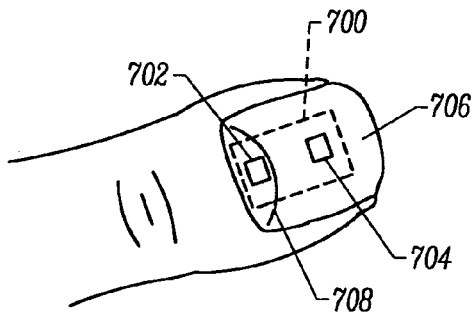
FIG. 7
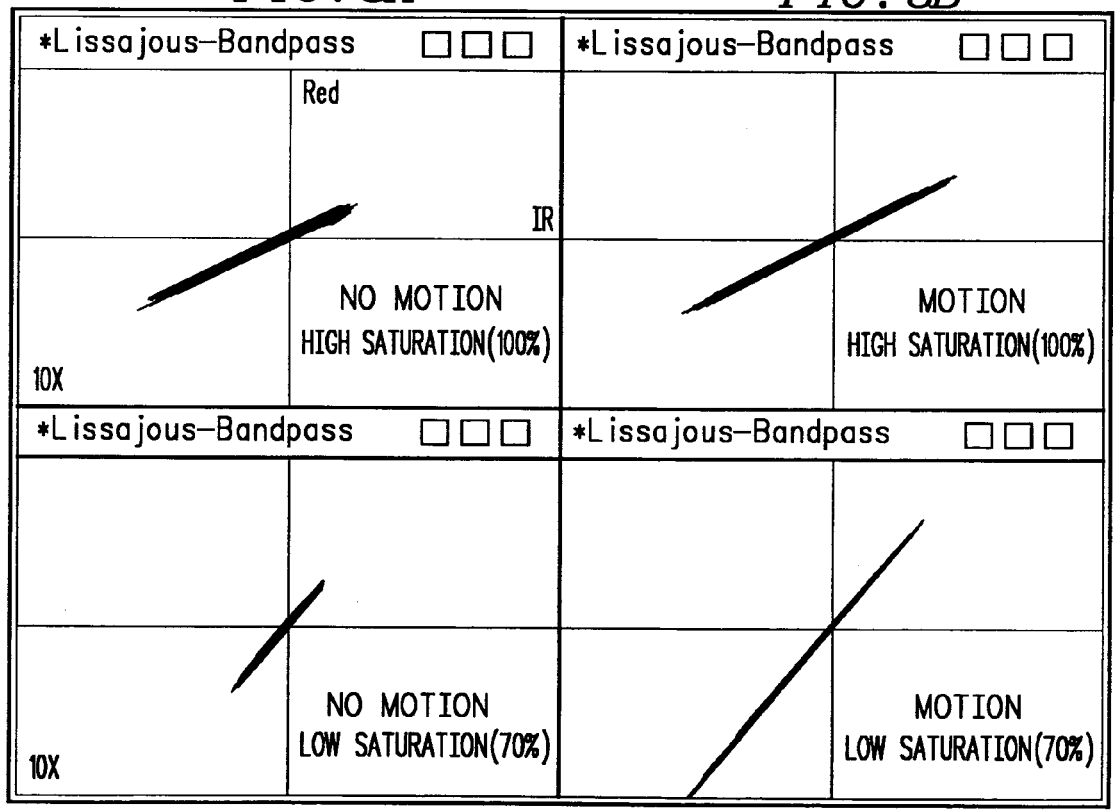
FIG. 8A  FIG. 8B
FIG. 8C  FIG. 8D

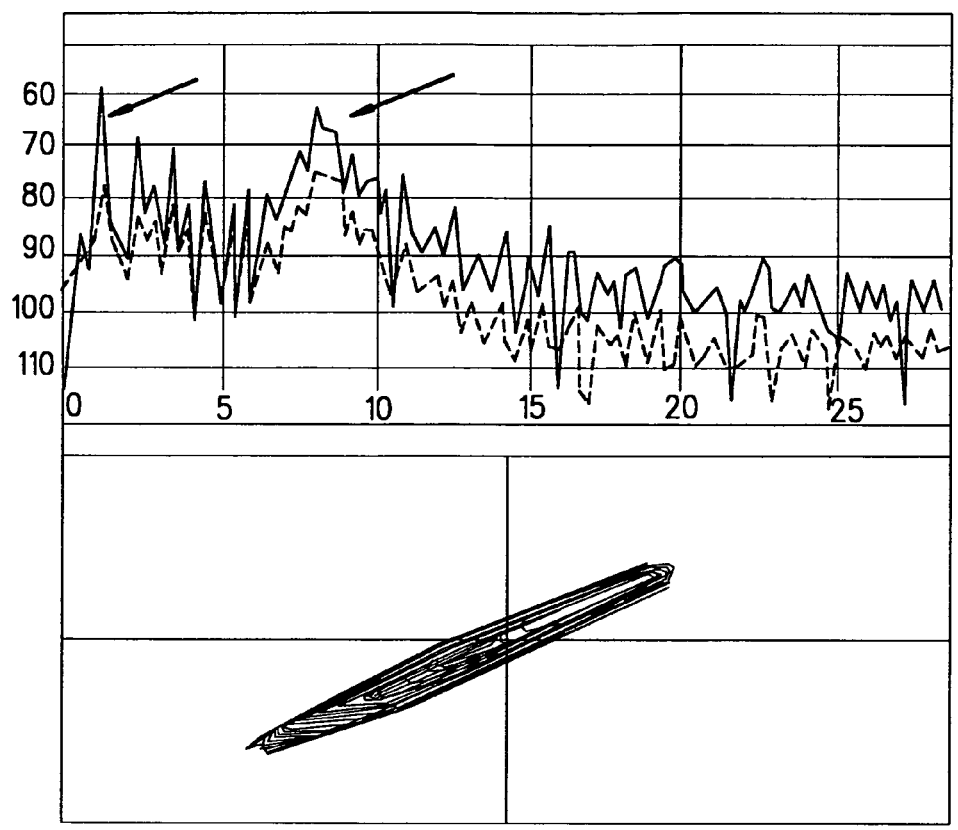
*FIG. 9A*
*FIG. 9B*
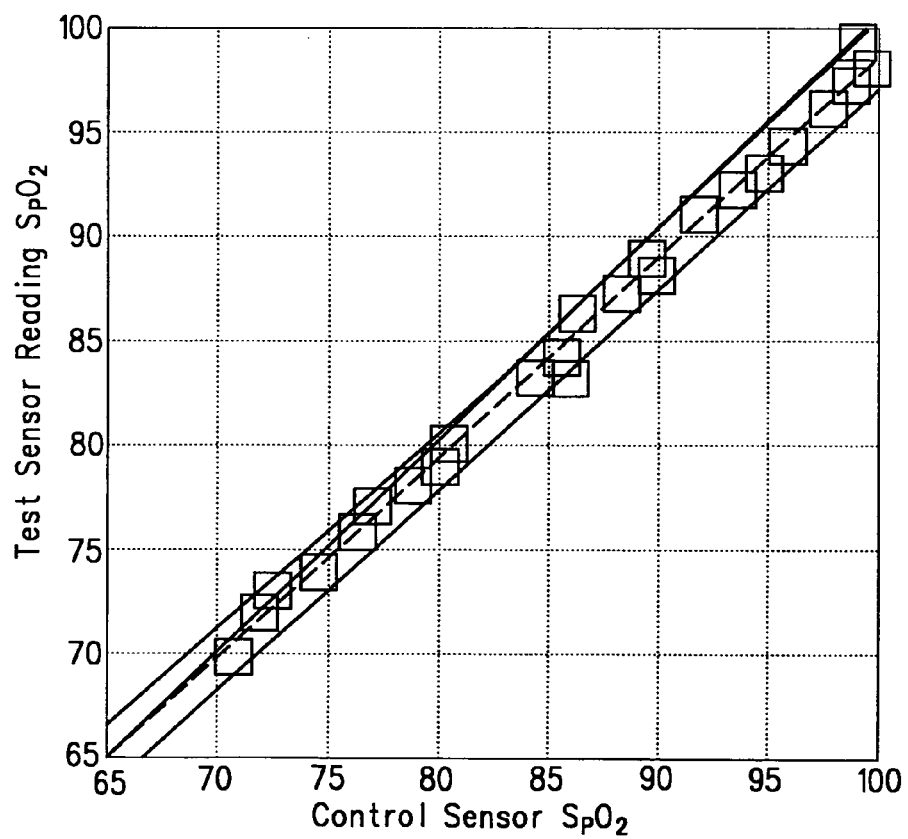
*FIG. 10*

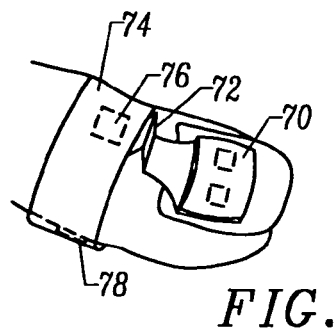
FIG. 12
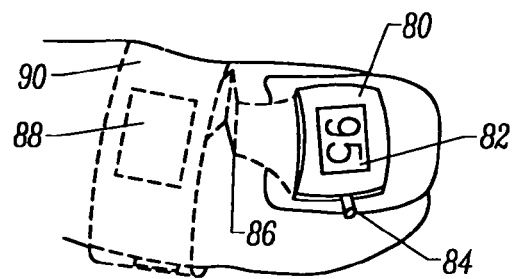
FIG. 13
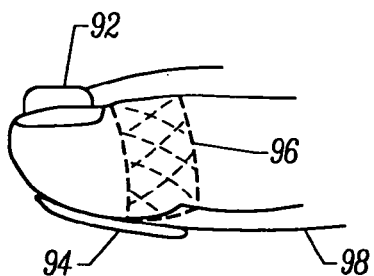
FIG. 14
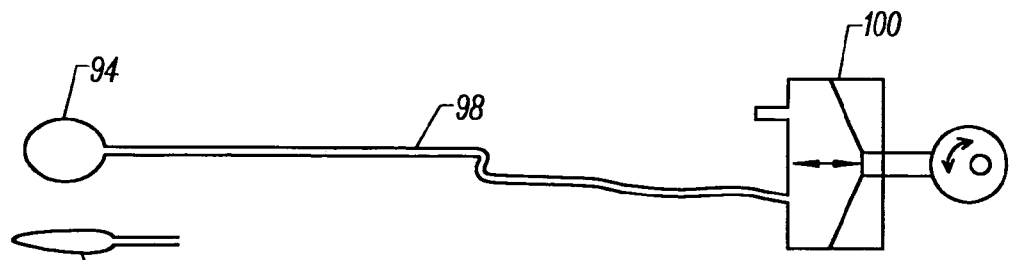
FIG. 15
FIG. 16

MOTION COMPATIBLE SENSOR FOR NON-INVASIVE OPTICAL BLOOD ANALYSIS

CROSS-REFERENCES TO RELATED APPLICATIONS

This application is a continuation of U.S. application Ser. No. 10/080,433, filed Feb. 21, 2002, now U.S. Pat. No. 6,845,256, which is a division of U.S. application Ser. No. 09/348,437, filed Jul. 7, 1999, now U.S. Pat. No. 6,374,129, which is a division of U.S. application Ser. No. 08/722,443, filed Oct. 10, 1996, now U.S. Pat. No. 6,018,673, which disclosures are incorporated by reference for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention relates to optical sensors for non-invasive determination of physiological characteristics, and in particular to sensors for making such determinations in the presence of motion.

Many types of optical sensors are used to measure physiological characteristics of a patient. Typically, an optical sensor provides emitted light which is then scattered through tissue and detected. Various characteristics of a patient can be determined from analyzing such light, such as oxygen saturation, pulse rate, pH, etc.

Pulse oximetry is typically used to measure various blood characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor. A photoelectric pulse transducer from World Precision Instruments is described as even recording signals through the fingernail.

Optical sensors are typically either reflective or transmissive. Transmissive sensors have the emitter and detector on opposite sides of a finger, toe, nose or other tissue. They measure light transmitted through the tissue from one side to the other. Reflectance sensors, on the other hand, have the emitter and detector side-by-side, such as placement on the forehead, or on a fetus where it is difficult to position a sensor over a finger, etc. Reflectance sensors detect light which is scattered back to the same surface.

In pulse oximetry, the goal is to determine the amount of oxygen in arterial blood, as distinguished from venous blood or the tissue itself. The light emitted can be absorbed by all three, however, and they need to be distinguished among. FIG. 1 illustrates a plot of the logarithm of the detected intensity signal versus time. Solid line 10 is the detected infrared signal in a pulse oximeter, shown varying with time. Dotted line 12 is the detected red wavelength signal. As can be seen, the value moves up and down with the heartbeat frequency, due to the pulsing of the blood through the arteries. The portion of the signal below line 14 is representative of light absorbed by the tissue, venous blood, and a baseline component of the arterial blood.

Using appropriate signal analysis, the DC portion can be eliminated, leaving an extracted AC portion which is due to absorption by arterial blood. As can be seen in FIG. 1, and more clearly in FIG. 2, the red and infrared signals, although varying by different amounts, are in phase. FIG. 2 illustrates a plot over an epoch of time of the red logarithmic signal versus the infrared logarithmic signal, and is commonly referred to as a Lissajous plot. As can be seen, a line is formed, indicating they are in phase.

This characteristic of the red and infrared signals allows the determination of oxygen saturation through two methods. In a first method, the "ratio of ratios" is calculated, which is the ratio, between red and infrared, of the logarithms of the quotients obtained by dividing the maximum signal intensity and the subsequent minimum signal intensity. This ratio-of-ratios is then used in a predetermined formula to calculate arterial oxygen saturation. This is described more fully in U.S. Pat. No. 4,653,498.

In a second method, referred to here as "least squares," a least squares regression analysis is performed on the above-mentioned Lissajous plot to determine the slope of the ensemble of data points taken during an epoch of time. This slope is then used in a predetermined formula to determine arterial oxygen saturation. Other techniques are set forth in a co-pending application entitled "Method and Apparatus for Estimating Physiological Parameters Using Model-Based Adaptive filtering," filed Jun. 7, 1996, Ser. No. 08/660,510, the disclosure of which is hereby incorporated by reference.

In some cases, it is desirable to measure the oxygen saturation of the venous blood in order to get an indication of how much oxygen is being used by the body. The arterial blood, on the other hand, gives an indication of how much oxygen is being delivered to the body. In Shiga U.S. Pat. No. 4,927,264, the oxygen saturation in venous blood is determined by inducing a venous pressure with a pressure cuff. This effectively varies line 14 of FIG. 1 at a frequency different from the heart rate, so that it can be separately filtered and isolated and compared to the arterial pulse. The non-varying portion is then assumed to be the tissue absorption and can be distinguished from the slowly varying pressure induced venous blood absorption. An alternate approach can be used in extracorporeal monitoring where the blood is actually pumped out of the body and then back in. Such a technique is set forth in an article by Odell et al., entitled "Use of Pulse Oximetry to Monitor Venous Saturation During Extracorporeal Life Support" Critical Care Medicine, vol. 22, no. 4 (Apr. 4, 1994). In Odell, the venous blood being pumped out of the body passes the sensor, and the pumping mechanism provides an artificial pulse allowing the use of pulse oximetry techniques.

Motion artifact can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Thus, typically techniques are employed to reduce the effects of motion or compensate for motion.

In one oximeter system described in U.S. Pat. No. 5,025,791, an accelerometer is used to detect motion. When motion is detected, readings influenced by motion are either eliminated or indicated as being corrupted. In a typical oximeter, measurements taken at the peaks and valleys of the blood pulse signal are used to calculate the desired characteristic. Motion can cause a false signal peak and valley, resulting in a measurement having an inaccurate value and one which is recorded at the wrong time. In U.S. Pat. No. 4,802,486, assigned to Nellcor Puritan Bennett, the assignee of the present invention, an EKG signal is monitored and correlated to the oximeter reading to provide synchronization to limit the effect of noise and motion artifact pulses on the oximeter readings. This reduces the chances of the oximeter locking onto a periodic motion signal. Still other systems, such as the one described in U.S. Pat. No. 5,078,136, assigned to Nellcor Puritan Bennett, use signal processing in an attempt to limit the effect of noise and motion artifact. The '136 patent, for instance, uses linear interpolation and rate of change techniques to analyze the oximeter signal. U.S. Pat. No. 5,337,744 sets forth sensor modifications used to improve the immunity of the signal from motion artifacts.

The motion signal impedes the measurement because it obscures the cardiac signal. The motion signal can have many components, such as, for example, the emitter or detector physically moving away from the body, or a volume of venous and arterial blood sloshing around in response to the motion, or the signal path being shortened or lengthened by expansion or compression of the tissue due to motion.

Contrary to conventional practice, signal analysis might be able to directly use the time-varying motion signal to calculate oxygen saturation. Under some conditions, the ratio-of-ratios (or least squares) resulting from a motion-induced signal has the same value as the ratio-of-ratios (or least squares) for the cardiac induced signal. The red and infrared intensity signals are often not in phase, and can limit the use of the motion signal for calculating oxygen saturation. One of the factors that may cause this is illustrated in FIG. 3. As FIG. 3 illustrates, light from emitter 28 can pass through skin 13, fat 15, muscle 16, and bone 18, on its way to a detector 30. Light of one wavelength may, on average, take path 32, while light of another wavelength may penetrate deeper and take path 34. Motion will cause disproportionate variances in the path lengths of the two wavelengths of light, resulting in out-of-phase signals of the detector.

BRIEF SUMMARY OF THE INVENTION

The present invention provides a non-invasive optical sensor which uses the motion signal to calculate the physiological characteristic being measured. For pulse oximetry, a least squares or a ratio-of-ratios technique can be applied to the slope of the motion signal itself. This is made possible by selecting a site on the patient where motion produces signals at two wavelengths which are adequately correlated with each other. Adequately correlated signals have a "closed" or "nearly closed" Lissajous. In particular, it has been determined that a sensor placed on a nail, in particular a thumbnail, exhibits the characteristics of having the red and infrared signals in phase when used for pulse oximetry.

The present invention also provides an optical sensor which fits entirely on a nail. No adhesive or other securing mechanism around the rest of the finger is necessary, resulting in the entire sensor moving with the nail. The use of the nail site reduces the likelihood of out-of-phase motion signals for red and infrared wavelengths, and takes advantage of the predominantly arterial blood saturation characteristic of the blood present beneath the nail. In addition, the nail is an advantageous surface for adhering the sensor to, and at this location the method of attachment allows a low profile, low mass sensor to be used which further limits differential phase errors due to motion.

Preferably, the sensor on a nail of the present invention is a reflectance-type sensor. In one embodiment, a closer spacing is used than in typical prior art sensors, preferably less than 5 mm, more preferably approximately 4 mm. It has been empirically determined that the physiological characteristics at a nail site produce an improved signal with closer spacing. In addition, the sensor preferably has a curvature which conforms to the shape of the nail, and is attached with an adhesive.

In alternate embodiments of the invention, artificial motion may be induced with an air bag or otherwise to produce a motion signal which can be used with the sensor of the invention. In particular, this could be used for patients with low perfusion, a weak heartbeat or no heartbeat such as is the case during heart bypass surgery.

For a further understanding of the nature and advantages of the invention, reference should be made to the following description taken in conjunction with the accompanying drawings.

BRIEF DESCRIPTION OF THE DRAWINGS

FIG. 7 is a diagram of a sensor according to the present invention placed longitudinally to span the lunula of the nail.

FIGS. 8A-8D are Lissajous plots of the output of a sensor according to the invention with and without motion, and at low and high saturation.

FIG. 9A is a plot of the red and infrared frequency distribution (FFT of time signals) showing experimental results from a thumbnail sensor according to the invention.

FIG. 9B is a plot of the Lissajous for the results of FIG. 9A.

FIG. 10 is a graph showing a plot of oxygen saturation readings of a sensor according to the present invention compared to a standard prior art sensor.

FIG. 12 is a diagram of an alternate embodiment of the invention showing a combination reflective and transmissive sensor.

FIG. 13 is a diagram of an alternate embodiment of the invention showing a self-contained nail sensor with its own display.

FIG. 14 is a diagram of a nail sensor with a motion inducing mechanism according to the present invention.

FIGS. 15 and 16 are top and side views of the motion stimulating mechanism of FIG. 14.

DETAILED DESCRIPTION OF THE INVENTION

Figure 4:
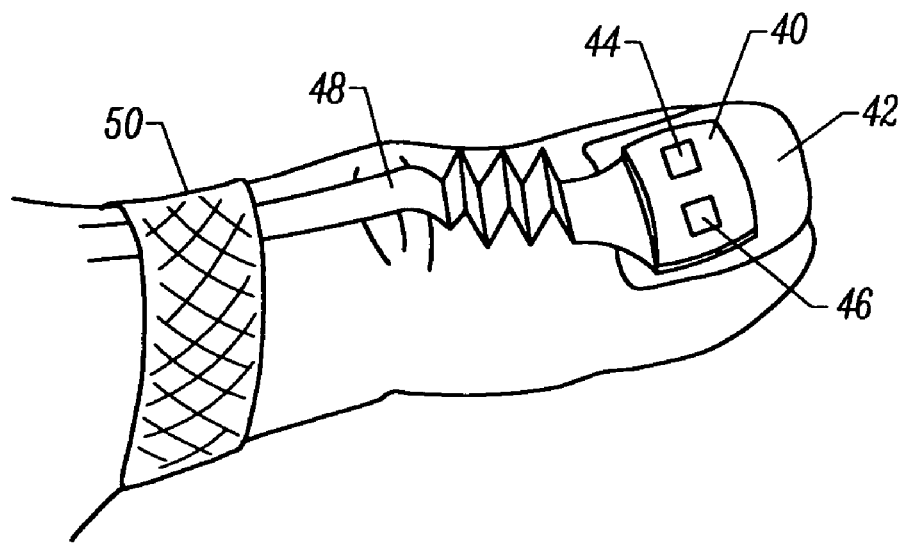
FIG. 4 is a perspective view of a nail sensor according to the present invention on a thumb.

FIG. 4 illustrates a sensor 40 according to the present invention preferably mounted on a nail 42 (a thumbnail or any other digit may be used). The sensor is held on with adhesive, and has an emitter 44 and a detector 46. A flexible circuit 48 provides the electrical connections to the emitter and detector, and may be accordion-shaped between the sensor and a securing band 50 to provide additional strain relief. This isolates the sensor from tugging or pulling on the electrical connection cord from either the sensor side or the other direction. Band 50 may be, for instance, an elastic band, cloth wrap secured with Velcro™, or another device. Flexible circuit 48 could be electrical wires or fiber optic cables. The different wavelength light could be premixed using the fiber optic cable.

The placement on the top of the nail allows the cable to extend along the top of the finger or other digit, without the sensor or the cable being on the palmar side of the digit where it would interfere with grasping or other functionality of the hand.

As can be seen, the emitter 44 and detector 46 are arranged laterally across the width of the nail. However, a longitudinal arrangement (discussed more fully below) or any other arrangement on a nail is possible. The spacing of the emitter and detector may be varied, but an optimum spacing was experimentally found to be less than 10 mm, preferably less than 5 mm, more preferably approximately 4 mm.

The nailbed makes a good site for the sensor because it has been observed that motion generates artifact signals for the red and infrared wavelengths that are largely correlated to one another. The inventors have observed that this results in a ratio-of-ratios (or least squares) which correlates well with the arterial oxygen saturation.

Figure 1:
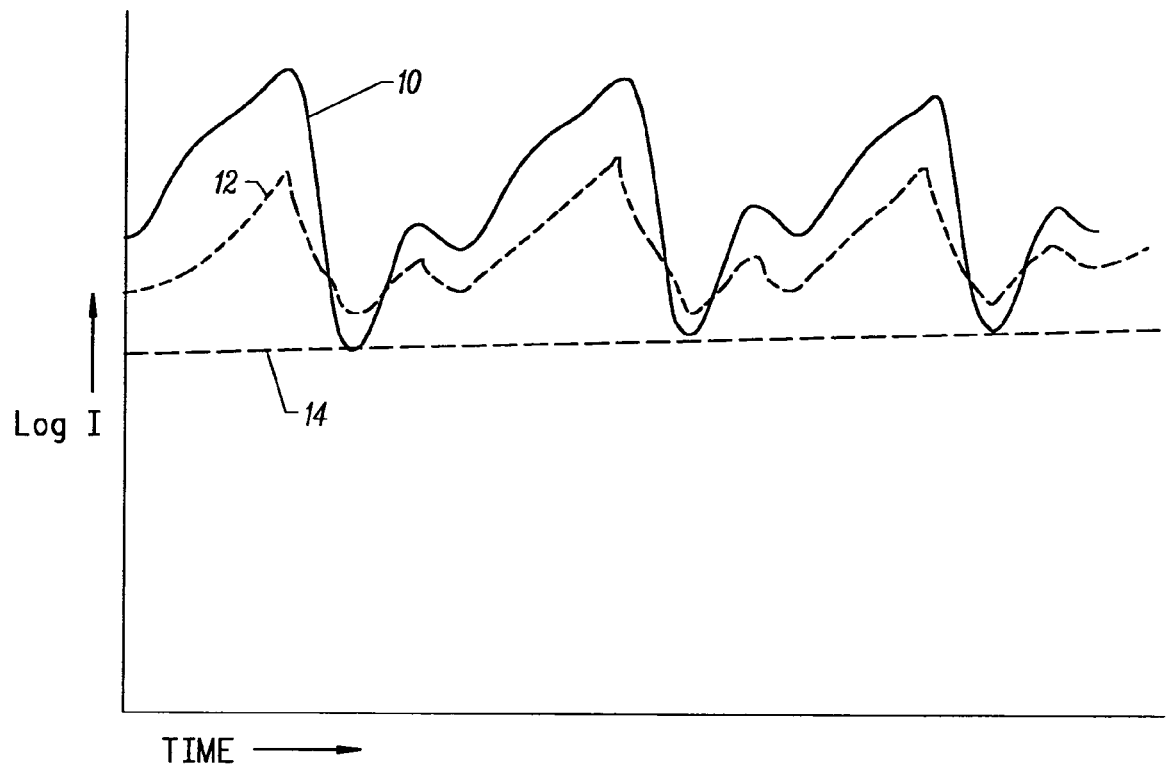
FIG. 1 is a graph of the log of the infrared and red intensity signals for pulse oximeters.
Figure 2:
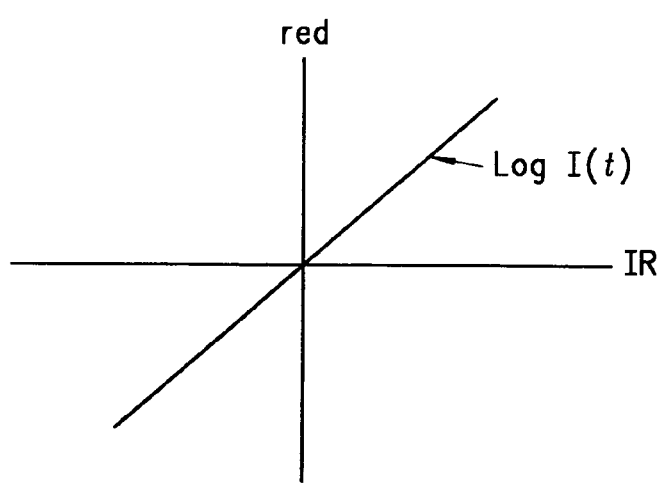
FIG. 2 is a graph of the red and IR signals showing correlation.
Figure 3:
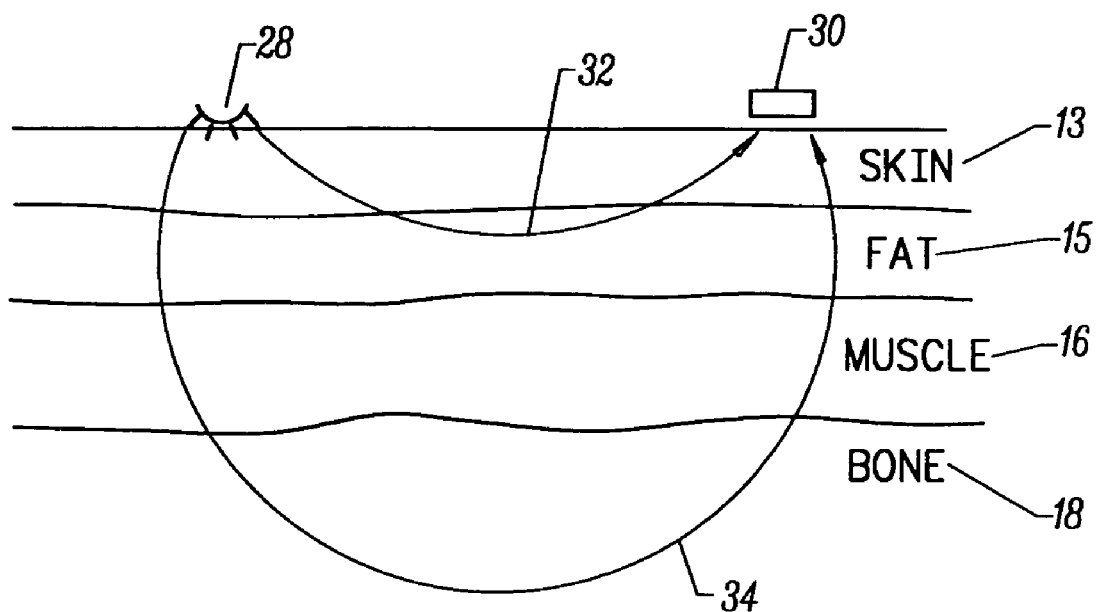
FIG. 3 is a diagram of the different average paths of different wavelength light through a patient.
Figure 5:
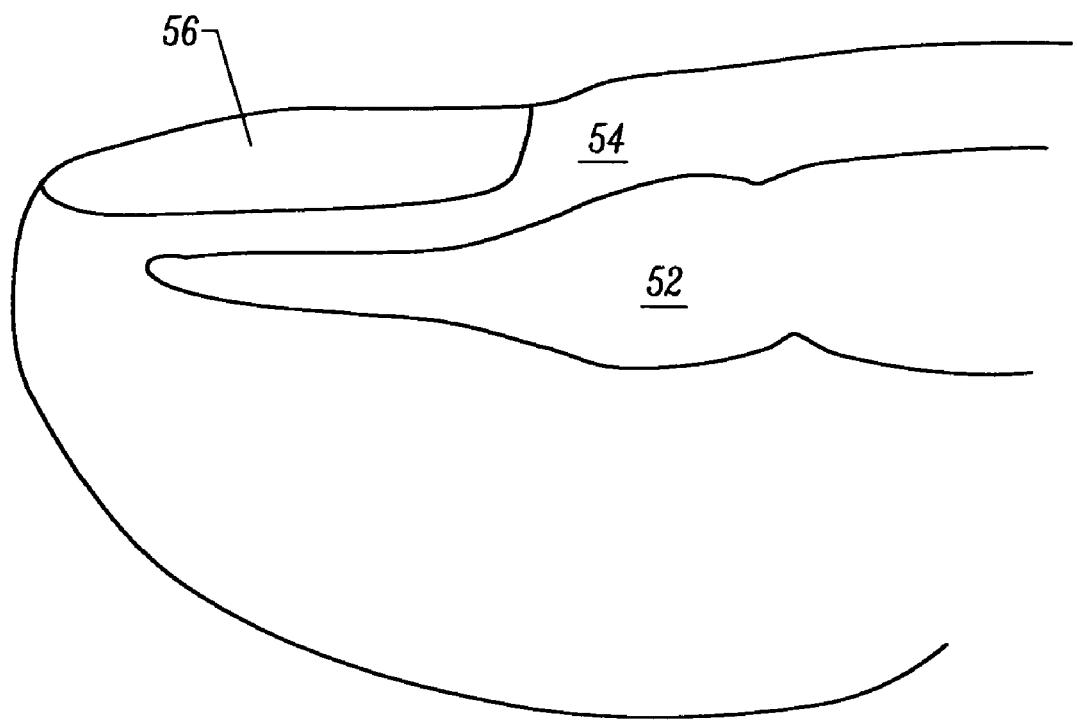
FIG. 5 is a cross-sectional, cutaway view of a thumb showing its components.

Referring to FIG. 5, a cross-sectional view of the thumb is shown. As can be seen, the thumb includes a bone 52 with a thin layer of connective tissue 54 between the bone and thumbnail 56. A number of characteristics may contribute to the improved signal and the motion induced artifact being in phase. The different wavelength paths illustrated in FIG. 3 may be limited by the presence of bone 52, preventing one of the wavelengths from going deeper into tissue and having a different distance to travel. This effect is provided by the selection of the thumbnail as a site, and the use of reflectance oximeter sensor as opposed to a transmissive sensor. In a transmissive sensor, light would have to travel around the bone deep through the tissue, and the red and infrared may travel different lengths and be affected differently by motion.

Connective tissue layer 54 is thin and apparently strongly connective. Thus, the expansion and compression of tissues, particularly fatty tissues, which may cause out of phase motion artifacts for other sites and types of sensors, is apparently greatly reduced here. Because the thumbnail 56 itself provides a strong mounting platform, the sensor can be securely attached to it with adhesive, avoiding the emitter and detector from separating from the patient and causing gaps that may cause corrupt ratio-of-ratio values.

The region beneath nail 56 also provides a region which appears to be concentrated with oxygen saturated blood similar to the saturation of arterial blood. Oxygen consumption beneath the nail appears to be small relative to the circulation there, or the relative volume of venous blood may be negligibly small.

The presence of many small capillaries, rather than large vessels, makes the region more homogeneous, and thus lessens the likelihood that two different light wavelengths would be affected differently by passing through differing regions. In the absence of motion, the high perfusion allows a normal pulse oximetry reading to be made. During the occurrence of motion, the large amount of blood present allows a strong motion signal to be obtained, since a lot of blood is moved around by the motion. In experiments conducted by the inventors, motion artifact signals greater than 50 times that of a normal pulsatile plethysmogram signal have been observed. The nail site also appears to have a nailbed-tissue boundary that is optically phase-matched for the wavelengths of the sensor.

In addition to measuring oxygen saturation, the nailbed is a good site for other optical sensors. For example, glucose detection which requires the use of a near infrared wavelength could be used. Among the blood properties or constituents that can be measured are blood gases ($CO_2$, $O_2$), pH, glucose, drug concentrations, or other analytes (THb, Hct, lactate, $K^+$, $Na^+$, $Ca_2^+$, etc.).

Figure 6:
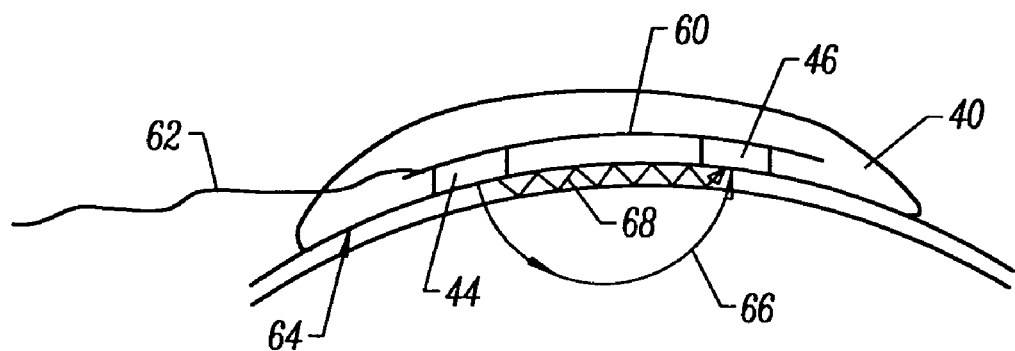
FIG. 6 is a end, cutaway view of one embodiment of a conformable nail sensor according to the present invention.

FIG. 6 is an end, cutaway view of one embodiment of a sensor 40 according to the present invention. Emitter 44 and detector 46 are shown mounted on a flexible circuit board 60. An electrical cord 62 provides the connection to the electrical components of circuit board 60. The body of the sensor is preferably a semi-rigid piece of black poron foam. A metal strip could be imbedded to give extra rigidity. An adhesive is attached to underside 64 of the sensor to attach it securely to the nail. The underside is also curved to conform to the shape of the nail, but is slightly flexible to allow adaptation to differing nail shapes. Different curvature sensors could be provided for different sizes and shapes of nails to provide optimum fit, or the bottom surface could be fabricated from a softer, more conforming material.

One characteristic of the nail as a site is that the nail itself could act as a light pipe, shunting light between the emitter and the detector. Preferably, the light travels through the tissue beneath the nail along a path 66. However, some light could bounce back and forth through the nail itself on a path 68 between the emitter and detector in a manner not unlike a waveguide. To limit this shunting, the sensor body is made to absorb light, or at least the region between the emitter and detector is made at least partially absorbing to the wavelengths of interest. In this way, each time light strikes the side of the nail adjacent the absorbing layer, it will be absorbed, rather than propagating along the nail.

Shunting can also be limited by recessing the emitter and detector and providing a narrow numerical aperture. Because of the rigidity of the sensor body, recessing will not produce variations in distance during motion. By limiting the numerical aperture of the emitter and detector to values less than 0.9, preferably to values less than 0.5, the emitter will not directly launch light into the nail "waveguide," and light which does potentially travel path 68 will be outside the acceptance angle of the detector.

The nail also provides advantages for adhering the sensor to the patient since the nail does not have the quantity of oils or sweat as present on the skin.

FIG. 7 is a diagram of a sensor 700 arranged longitudinally along a nail 706. The sensor has an emitter 702 and a detector 704 which are not both on the lunula of the nail. The lunula is the light colored area of the nail below line 708 in FIG. 7. It is believed that if both the emitter and detector are located on the lunula, more undesirable shunting of light will occur.

FIG. 8 has FIGS. 8A-8D which show the Lissajous plots and calculated saturations for a sensor according to the present invention during four conditions: motion and no motion at high and low saturation. As can be seen in FIGS. 8A and 8B at high saturation, the calculated saturation 100% is equivalent with or without motion. In FIG. 8B, the motion signal is seen to be more than 10 times larger than the cardiac signal of FIG. 8A (FIGS. 8A and 8C are magnified by 10). Similar results occur at low saturation as seen in FIGS. 8C and 8D where the saturation values are calculated to be 70% under both conditions.

FIG. 9A is a graph of the frequency distribution of the detected red and infrared signals for a sensor of the present invention in an experiment with an 8 Hz artificial motion pulse applied. The cardiac signature can be seen at the lower frequencies below 5 Hz, while the 8 Hz driven motion signal is also visible. FIG. 9B is a graph of the red versus infrared intensity signals for the experiment illustrating that both signals are correlated and representative of the same saturation.

FIG. 10 illustrates the oxygen saturation readings of a sensor according to the present invention in experimental tests without motion comparing it with a standard prior art transmissive sensor at another site. A close agreement was noted, indicating the calibration of this sensor on the nailbed site is similar to a conventional transmission sensor.

Figure 11A:
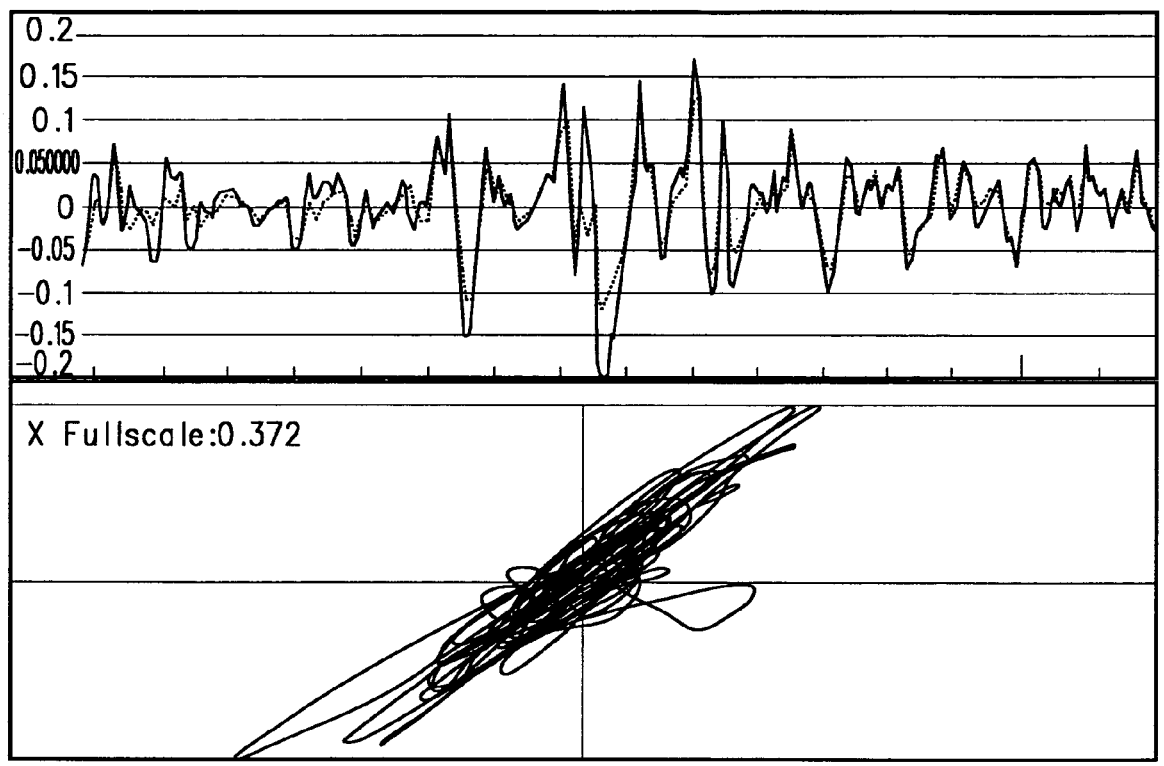
FIGS. 11A and 11B compare the prior art sensor and the present invention. The output waveforms and Lissajous plot are shown for each.
Figure 11B:
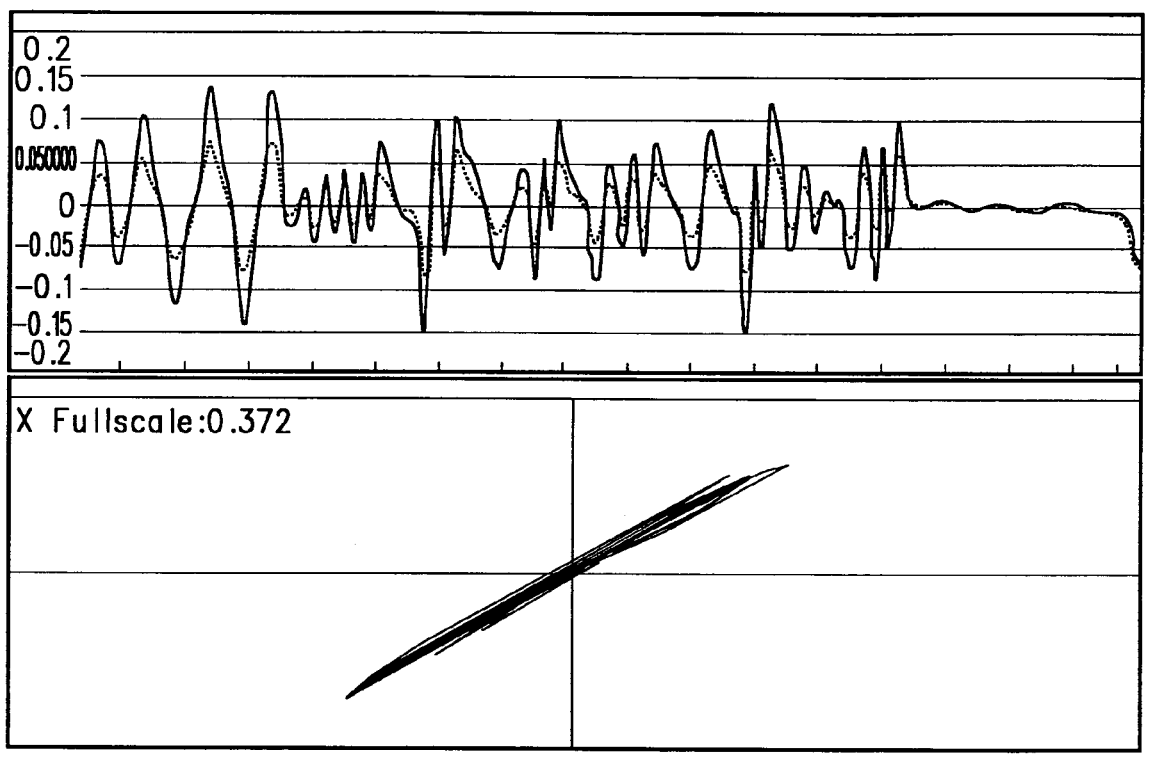

FIGS. 11A and 11B show a comparison of the output waveform and Lissajous, in the presence of motion, of a sensor according to the present invention (FIG. 11B) with a standard prior art transmissive sensor at another site (FIG. 11A).

FIG. 12 illustrates an alternate embodiment of the present invention in which a nail sensor 70 according to the present invention is attached via a flexible circuit 72 to a transmissive sensor 74 which wraps around the finger and has an emitter 76 and detector 78 positioned on top and on the bottom of the finger. Such a combination sensor could allow the oximeter monitor with its program to choose between the sensors depending upon motion conditions. When motion is present, nail sensor 70 could be used, and when motion is not present, sensor 74, which may be more sensitive to the cardiac pulse signal, could be used. Alternately, a single pair of red and infrared emitters could be used, with a reflectance detector on the nail, and a transmissive detector off the nail. Depending on the mode, a switch in the sensor, or in an intermediate amplifier module, or in the oximeter monitor could select between the detectors. In another embodiment, a single detector is used, with one pair of emitters on the nail, and another pair of emitters off the nail. Alternately, a completely separate transmissive sensor could be used.

In some patients, in particular those with low blood perfusion, it may be difficult to lock onto a pulse waveform. The additional transmissive sensor could be used to enable locking on for such patients. In addition, a transmissive sensor could be used to calibrate the nail sensor "on-the-fly." Because of shunting and other unique aspects of the nail site, a predetermined calibration may be off. A measurement of saturation using the transmissive and the nail reflectance sensors could be done in the absence of motion, with a correction factor applied to the reflectance sensor. The correction could be a constant which is added or a multiplicative factor, or both. If measurements are done at different saturations, a calibration line or curve could be determined by the oximeter to allow adjustments anywhere along the calculated curve. Subsequently, in the presence of motion, the nail sensor will be more accurately calibrated.

FIG. 13 illustrates an alternate embodiment of the invention in which a self-contained sensor 80 according to the present invention includes the processing circuitry on one or more semiconductor chips inside, and has its own display 82, which may be a liquid crystal display, for instance. In one embodiment, a button 84 allows switching between modes, such as between displaying a pulse and oxygen saturation. In an alternate embodiment, a flex connection 86 to a module 88 attached on a band 90 may be used. Module 88 might contain the battery, or alternately the processing circuitry, or the display. Additionally, either embodiment could be used for a wireless transmission to an oximeter, with the transmitting circuit either being in module 88 or sensor body 80.

FIG. 14 illustrates another embodiment of the present invention in which a stimulator is used to generate an artificial pulse. A stimulator could electrically stimulate the nerves to cause motion of an appendage, or could use a pneumatic pressure cuff to stimulate an artificial pulse, or use electro-mechanical stimulation or any other mechanism which generates a pulse characteristically different (e.g., amplitude, frequency, shape, etc.) than the cardiac pulse so that the cardiac pulse need not be used. Such an apparatus would be particularly advantageous for patients with low blood perfusion or a weak heartbeat. FIG. 14 is one embodiment showing a sensor 92 mounted on a thumbnail, with an airbag 94 mounted to the bottom of the thumb and held in place with a band 96. A hose 98 to the airbag periodically inflates and deflates it, causing a pressure wave through the thumb, giving artificially induced motion. This pressure induced motion provides the variation needed for sensor 92 to measure the oxygen saturation using either the ratio-of-ratios or a least squares technique. If the motion is in the frequency range of a heartbeat, the sensor can be backward compatible with existing oximeter monitors, even those that look for a cardiac signal.

FIG. 15 illustrates airbag 94 in a top view, showing hose 98 connected to a diaphragm pump 100. FIG. 16 shows a side view of the airbag 94 of FIG. 15, showing that it is wide but flat.

Figure 17:
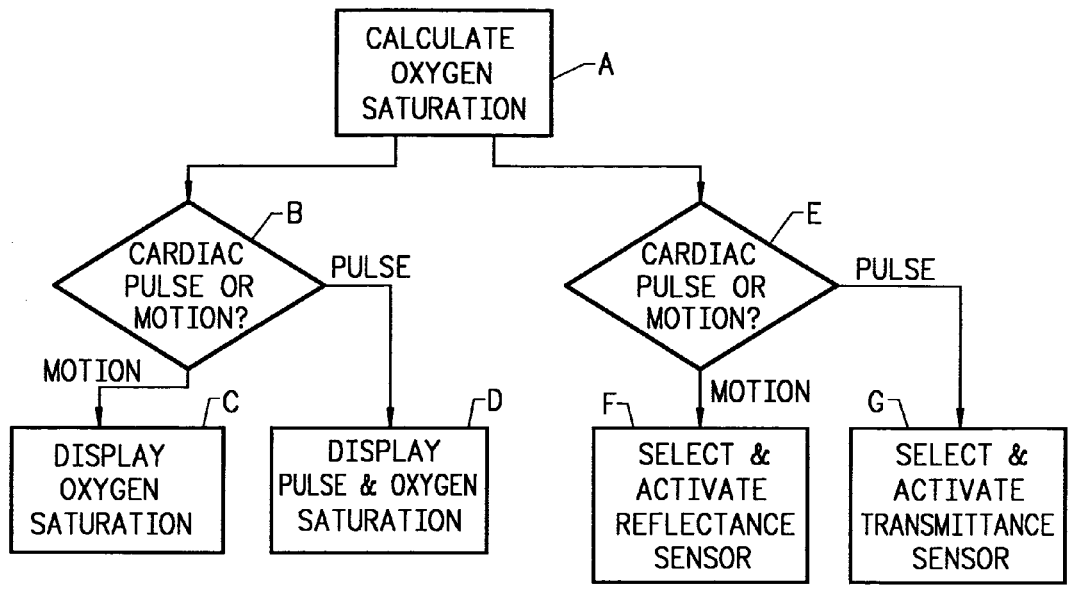
FIG. 17 is a flowchart of one embodiment of a program for responding to whether motion or a cardiac pulse is used for calculating saturation.

FIG. 17 is a flowchart of one embodiment of a portion of a program for operating an oximeter so that either cardiac pulses or motion pulses can be used to calculate oxygen saturation. The oxygen saturation is calculated in a known manner (step A). In a first alternative, the signal is analyzed to determine if it is a cardiac pulse or a motion pulse (step B). This can be done using any of the pulse qualification or motion detection techniques known to those of skill in the art. If a motion signal is present and used for the oxygen saturation calculation, then in step C only the oxygen saturation signal is displayed, and not a pulse rate (which would be a motion pulse rate, and not the patient's heart rate). If a cardiac pulse is used, the pulse rate is also displayed (step D).

Alternately, a pulse determination step E could be used where the sensor includes both a reflectance sensor and a transmittance sensor. If motion is present above a predetermined threshold (such as at least twice the arterial pulse signal), the reflectance sensor is used, which uses the motion signal, and alters any motion filtering or motion reduction techniques (step F). If the motion signal is below the threshold, the transmittance sensor is used (step G), with standard motion reduction techniques being employed (either hardware or software or both).

Both sensors could be energized in an ongoing manner, and the saturation and rate could be chosen to come from the sensor considered most reliable, depending on the instrument's assessment of motion. Simultaneous computation may further allow improved processed signal estimates of cardiac rate in the presence of motion given knowledge of estimated saturation.

Figure 18:
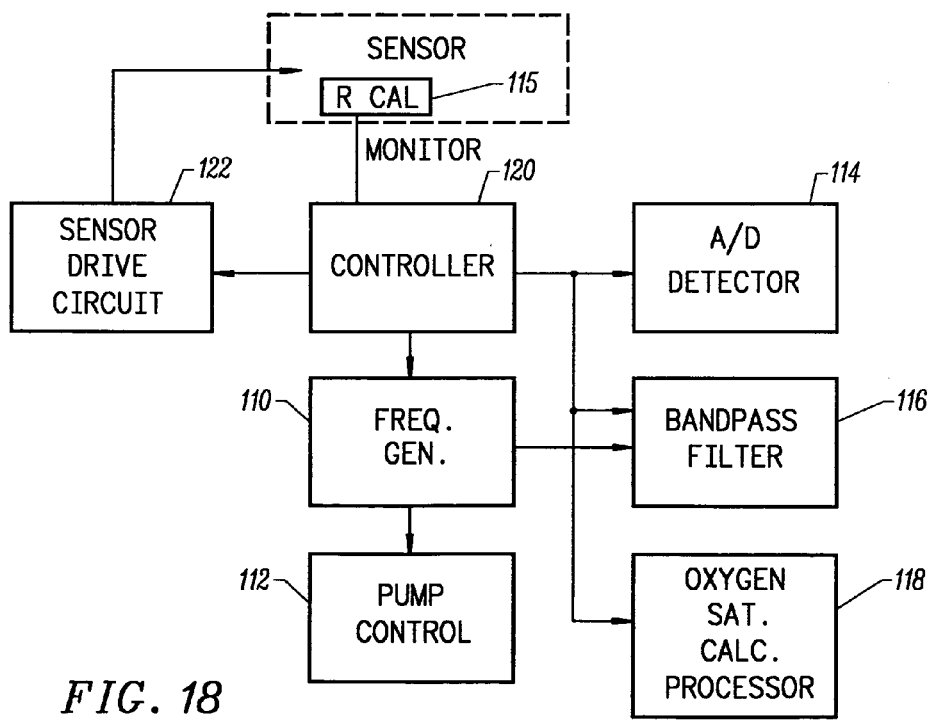
FIG. 18 is a block diagram of one embodiment of portions of an oximeter using controlled generation of motion.

FIG. 18 is a block diagram of a portion of a pulse oximeter monitor used in conjunction with an artificial pulse generator, such as shown in FIGS. 14-16. A frequency generator 110 produces a desired frequency for the motion pulse. This could be varied to give a frequency which is not interfered with by other noise, or frequency hopping could be used to isolate the signal from other sources of motion or noise. A pump controller 112 activates a pump or motor 100 (FIG. 12) at the generated frequency. Since the driven frequency is known, optionally other frequencies could be filtered out to reduce noise. After a signal is captured and converted to digital form by a circuit 114, a bandpass filter 116 is used to reduce other frequency signals. A control signal from frequency generator 110 could vary the bandpass frequency. A circuit or processor 118 then calculates the oxygen saturation. A central controller 120 controls the rest of the circuitry, including a sensor driver circuit 122, which could selectively activate different reflectance and transmittance emitters in one embodiment. Controller 120 could also analyze the signals for the presence of motion to alternate between motion and cardiac pulse modes in one embodiment. Alternately, a separate motion sensor could provide an input to controller 120. Note that other physical implementations are possible, such as using a single processor to do the filtering, the frequency generation and the oxygen saturation calculation.

A calibration resistor (or other active or passive element) 115 encodes the mean wavelength of at least one LED, and provides it to a calibration reader circuit or CPU 120. The wavelength indicated is used to select coefficients stored in the monitor. Such a calibration technique is described in more detail in U.S. Pat. No. 4,621,643, the disclosure of which is incorporated herein by reference.

Figure 19:
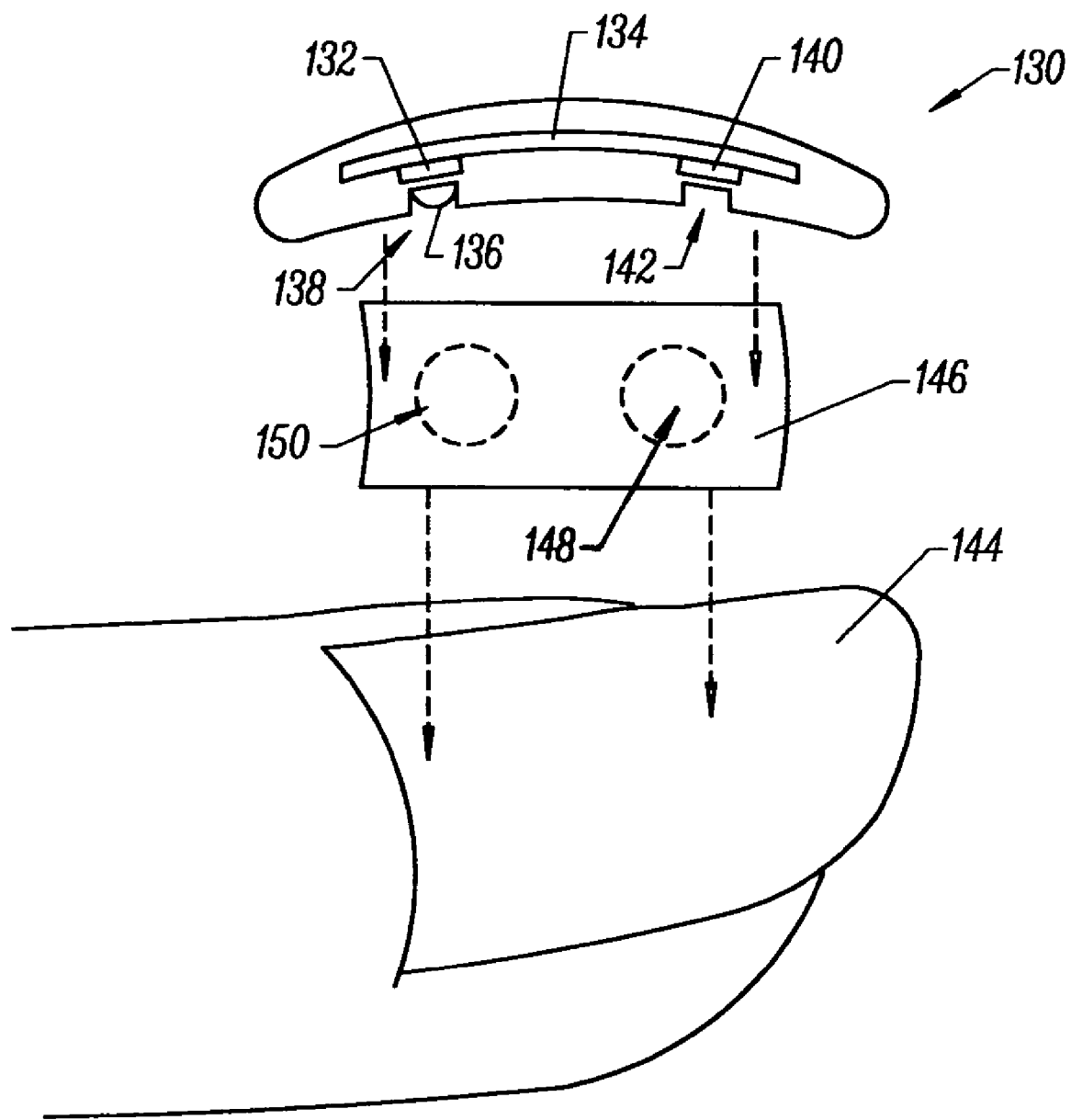
FIG. 19 is a diagram of an embodiment of the sensor using a cylindrical lens and a tinted adhesive.

FIG. 19 is a cut-away view of an embodiment of a sensor 130 according to the invention. An emitter 132 is mounted on a circuit 134 inside the sensor housing. A cylindrical lens 136 is mounted in an aperture 138. The lens directs the light down through the nail, minimizing the light which hits the nail at an angle and can be shunted to the detector. An aperture itself can perform the same function, but the lens insures that more of the light is used, maintaining a higher intensity at a given power, or allowing less power to be used. Detector 140 is recessed in an aperture 142 to avoid shunted light on the receiving end.

The sensor is secured to a nail 144 using an adhesive layer 146. The adhesive layer can act as a shunt path itself. Accordingly, the adhesive layer may be tinted to be opaque to the wavelengths used, with preferably transparent windows 148 and 150 for the detector and emitter apertures.

As will be understood by those of skill in the art, the present invention could be embodied in other specific forms without departing from the spirit or essential characteristics thereof. For example, a sensor could be placed on a fingernail other than the thumb nail, and could be placed on toenails. Alternately, a sensor could be placed on the cuticle or the live nail fold skin extending over the beginning of the nail. The sensor could be attached with a clip-type sensor, or an elastic wrap, bandage or adhesive which encircles the appendage could be used. The sensor could be placed at locations other than the nailbed where signals at the multiple wavelengths in the presence of motion are still adequately correlated. The emitter in the sensor could be fabricated using an optical fiber to carry the light from a source remotely located, and equivalently the detector could be an optical light guide to pipe the light to a remote detector. Accordingly, reference should be made to the following claims which set forth the scope of the invention.

What is claimed is:

1. A photometric processing device for processing detector signals from a radiation detector in a patient sensor also having a radiation emitter, comprising:
    a first processing unit configured to determine a blood parameter from a cardiac signal derived plethysmogram from the detector;
    a second processing unit configured to determine the blood parameter from a motion artifact waveform from the detector; and
    a control unit configured to utilize the first and second processing units responsive to a motion artifact content of the detector signals.

2. The photometric processing device of claim 1 further comprising a processor and a memory, wherein the first and second processing units and the control unit are first, second and third programs stored in the memory.

3. The photometric processing device of claim 1 further comprising a selector configured to select between a reflectance mode and a transmittance mode of the sensor.

4. The photometric processing device of claim 3 wherein the control unit is further configured to switch between the first and second processing units in accordance with a selection of the selector.

5. The photometric processing device of claim 4 wherein the selector is responsive to the motion artifact content of the detector signals.

6. The photometric processing device of claim 1 wherein the radiation emitter emits and the radiation detector detects radiation at two or more wavelengths, wherein the detector signals at the two or more wavelengths are correlated in the presence of motion.

7. The photometric processing device of claim 6 wherein the detector signals produce a closed Lissajous.

8. The photometric processing device of claim 1 wherein the detector signals are generated in response to at least two wavelengths and are correlated in the presence of non-cardiac pulses.

9. The photometric processing device of claim 8 wherein the detector signals include predominately motion-induced variations and the sensor is configured to be placed on a nail on a digit.

* * * * *